United States Patent [19]

Lampson et al.

[11] 4,124,702

[45] Nov. 7, 1978

[54] POLYNUCLEOTIDES ACTIVE AS INDUCERS OF INTERFERON PRODUCTION IN LIVING ANIMAL CELLS

[75] Inventors: George P. Lampson, Hatfield; Alfred A. Tytell, Lansdale; Arthur K. Field, North Wales; Maurice R. Hilleman, Lafayette Hill, all of Pa.

[73] Assignee: Merck & Co., Inc., Rahway, N.J.

[21] Appl. No.: 750,499

[22] Filed: Dec. 14, 1976

Related U.S. Application Data

[63] Continuation of Ser. No. 160,188, Jul. 6, 1971, abandoned, which is a continuation of Ser. No. 684,936, Nov. 22, 1967, abandoned, which is a continuation-in-part of Ser. No. 659,308, Oct. 9, 1967, abandoned, which is a continuation-in-part of Ser. No. 641,119, May 25, 1967, abandoned, which is a continuation-in-part of Ser. No. 604,137, Dec. 23, 1966, abandoned.

[51] Int. Cl.$^2$ .............................................. A61K 45/04
[52] U.S. Cl. ........................................ 424/85; 536/28
[58] Field of Search ........................................... 424/85

[56] References Cited

U.S. PATENT DOCUMENTS

3,629,235  12/1971  Lampson et al. ................. 260/211.5

OTHER PUBLICATIONS

Finter *Interferons*, published by North-Holland Pub. Co., Amsterdam, 1966, pp. 36, 37 and 256.
Hilleman *Arch. Intern. Med.*, vol. 126, pp. 114, 119, and 120, (1970).
Lampson et al., *Proc. Nat. Acad. Sci.*, vol. 58, pp. 782-789 (1967).
Langridge et al., *Proc. Nat. Acad. Sci.*, vol. 52, pp. 114-119 (1964).
Weissmann et al., *Proc. Nat. Acad. Sci.*, vol. 51, pp. 682-690 (1964).
Iglewski et al., *J. Virol.*, vol. 1, pp. 302-307, Apr. 1967.
Haselkorn et al., *J. Biol. Chem.*, vol. 236, pp. 2738-2745 (1961).
Rotem Israel, *J. Exper. Med.*, vol. 11, pp. 174-178 (1963).
Lancet, Mar. 6, 1965, pp. 505 and 506.

*Primary Examiner*—Shep K. Rose
*Attorney, Agent, or Firm*—Walter Patton; Harry E. Westlake, Jr.

[57] ABSTRACT

Polynucleotides which are multistranded are active as inducers of interferon production in living animal cells. They may be:
a. Synthetically complexed polymers of two homopolynucleotides.
b. A nucleic acid released by phenol from a ribonucleic acid complex elaborated by the growth of *Penicillium funiculosum*.
c. A ribonucleic acid from reovirus type 3 virions.
d. Replicative forms of nucleic acids.

3 Claims, No Drawings ically defined, non-toxic, non-antigenic, non-replicating, synthetic agents that can be prepared from readily available homopolynucleotides. The mode of administration of the complexed polymer can be either parenterally, such as subcutaneously, intradermally, intraperitoneally, intravenously, intramuscularly, orally, or topically, preferably on a mucous membrane such as intranasally. These complexed polymers are produced on admixture of two different homopolynucleotides which themselves are synthetic and comercially available, and can be made by established procedures.

POLYNUCLEOTIDES ACTIVE AS INDUCERS OF INTERFERON PRODUCTION IN LIVING ANIMAL CELLS

CROSS-REFERENCE TO RELATED CASES

This is a continuation of application Ser. No. 160,188, filed July 6, 1971, which is a continuation of application Ser. No. 684,936, filed Nov. 22, 1967, which is a continuation-in-part of application Ser. No. 604,137, filed Dec. 23, 1966, now abandoned, Ser. No. 641,119, filed May 25, 1967, now abandoned, and Ser. No. 659,308, filed Oct. 9, 1967, now abandoned.

This invention relates to substances which will induce living cells to produce interferon and, particularly, the invention involves the discovery that multistranded polynucleotides and especially ribonucleic acids (RNA) have exceptional properties as interferon inducers.

Interferons are proteins of relatively low molecular weight which are produced by cells and it is known that this production is stimulated by viruses, certain other microbial agents, and by several substances of various origin. The interferons impart resistance to viral infection in uninfected cells for prolonged periods of time when give prior to virus. They are broad-spectrum with respect to virus species but are relatively host species-specific.

The polynucleotides of this invention can be used as an inducer for interferon production, either in vivo or in vitro. The principal use is its injection into an animal or a person so that interferon is produced in vivo in large quantities whereby it serves to protect the host against infection by a variety of viruses. It is also useful, although perhaps to a lesser degree, for addition to a culture medium containing living animal or human cells as it serves to induce the formation of interferon in large quantities so that the interferon can be recovered for injection into that animal species or man to increase resistance to a virus infection.

The interferons appear to be responsible, in part at least, for recovery from infection in the early stages and appear to provide at least one mechanism for the interference phenomenon. A feature of the present invention is the provision of interferon inducers which may be administered to animals and humans whereby the body will be stimulated to make its own interferon. Our present discovery is that certain polynucleotides are highly active in inducing interferon and host resistance but that such activities are dependent upon 2 conditions: (a) high degree of purity, i.e. substantially free from inhibitory protein and/or other inhibitory substances and (b) multistrandedness of the polynucleotides. Certain ribonucleoproteins and single-stranded polynucleotides have been found to be inactive.

The multistranded polynucleotides in this invention may be obtained from several sources and these include, (A) those resulting from the complexing of certain synthetic polynucleotides to become active as interferon inducers, (B) a ribonucleic acid, hereinafter called HeI-RNA, produced by mixing an extract of *Penicillium funiculosum* with phenol to obtain a release of the interferon inducing RNA which is then recovered in a highly purified form, (C) a ribonucleic acid obtained from reovirus type 3 virions, and (D) a replicative form of ribonucleic acid obtained by infecting living cells with a RNA virus.

These representative sources of the multistranded RNA and its recovery and use are described as follows:

(A) COMPLEX OF SYNTHETIC POLYNUCLEOTIDES

This feature of the invention involves the discovery that interferons can be induced in a host animal by administration of complexed polymers which are chemically defined, non-toxic, non-antigenic, non-replicating, synthetic agents that can be prepared from readily available homopolynucleotides. The mode of administration of the complexed polymer can be either parenterally, such as subcutaneously, intradermally, intraperitoneally, intravenously, intramuscularly, orally, or topically, preferably on a mucous membrane such as intranasally. These complexed polymers are produced on admixture of two different homopolynucleotides which themselves are synthetic and comercially available, and can be made by established procedures.

In the following discussion and claims, the term homopolynucleotide will be used to include not only the homopolynucleotides but also the homooligonucleotides, the difference being only in the length of the polymer; that is, it will embrace polymers having from two to thousands of nucleotide units. These known polymers are prepared by enzymatically treating nucleotide diphosphates or triphosphates in vitro to form the desired polynucleotide in varying numbers of nucleotide units, the number of which cannot be known with precision.

The synthetic homopolynucleotides employed in the preparation of the complexed polymers have a pentose-phosphate skeleton, preferably wherein the pentose is ribose or deoxyribose, as well as a specific identifiable pyridmidine or purine base such as adenine, inosine, cytosine, uracil, guanine and the like. The prior art teaches that mixing of certain homopolynucleotides in aqueous solution results in the formation of a complexed polymer identifiable through various physical tests and which is different from either of the two homopolynucleotides from which the complexed polymer is formed. The ratio in which the two homopolynucleotides are mixed is normally not controlling as to the ratio of the two homopolynucleotides incorporated in the complex. A mixture in a 1:1 molar ratio can result in a complexed polymer containing the two nitrogenous bases in a 1:1, 1:2, and/or 2:1 ratio or some other ratio of small whole numbers, that is, the resultant ratio is not a function of the ratio in which the components are mixed but is determined by some natural propensity to so combine which is peculiar to the particular homopolynucleotides employed.

The complexed polymers employed as interferon inducers in the present invention are prepared, for example, by mixing two dissimilar homopolynucleotides in a 1:1 molar ratio with respect to their bases at ambient temperature in an aqueous buffer system having a broad pH range, i.e., between about 5.0–10.0, and an ionic strength of between about 0.001–1.0. Ratios other than 1:1 can be used as indicated above. Buffer systems that have been found useful are 0.006M sodium phosphate in 0.85% sodium chloride solution and 0.01M glycyl-glycine in 0.59% sodium chloride. Any non-toxic buffer can be used, or indeed no buffer need be used, since it has been found that the buffer capacity of the physiological system of the animal to which the mixture of homopolynucleotides is to be administered is satisfactory to promote the desired complex formation after administration and provide the same induction of interferon production and protection from viral infection as when the two homopolynucleotides are precomplexed.

Another method for the preparation of complexed polymers that can be employed is to treat a mixture of two nucleotide-diphosphates or deoxynucleotide-triphosphates in a phosphate buffer of about pH 7, with the appropriate nucleic acid polymerase, or deoxynucleic acid polymerase. Such treatment results in polymerization of the two monomers to two homopolynucleotides with concomitant formation of the complexed polymer.

The complexed polymers formed in vitro can be characterized by a hypochromic shift in the ultraviolet absorption spectrum, sucrose density gradient fractionation, chromatography, and the capacity to induce the production of interferon, an activity which is lacking in either of the homopolynucleotides from which the complex is formed. The production of interferon serves most significantly to characterize the complexed polymers used in the process of this invention since physical methods often lack sufficient sensitivity.

The production of interferon by administration of the complexed polymers is demonstrated by the protection of host animals as well as cell cultures from virus challenge. The interferon so produced also can be characterized by isolation of the induced interferon by known methods followed by in vitro determination of its viral inhibiting properties and characterization by host specificity, trypsin sensitivity, isoelectric point and molecular weight determination.

The induction of interferon formation in vivo and/or the induction of resistance to viral infection, according to this feature of the invention is achieved by administration of a complexed polymer, prepared as described above, to a host animal such as a rabbit, mouse, or other animal. The administration can be parenteral or superficial particularly to a mucous membrane, such as intranasal, and the effective dose depends on the host species and to some extent on the virus against which the protection is sought. In mice the threshold dose is about 0.5 mg/kg whereas in rabbits it is approximately 0.05 μg/kg. At these doses there are no overt signs of toxicity either locally at the site of injection or generally in the well-being of the whole animal. The effectiveness of the complexed polymers in inducing interferon formation in the host animal can be determined, inter alia, by parenteral administration of the complexed polymer to an animal and after about 1 to 5 hours taking blood samples. The serum is separated from clotted samples of the blood, sterilized, and titrated at several dilutions in culture tubes containing cells from the same animal species as that used for host. After incubation at 35° C. for about 18 to 24 hours the cell cultures are challenged with any one of the known cytopathic viruses and again incubated at 35° C. for about 3 days. The cultures then are examined for cytopathic effects and the interferon titer is determined as the reciprocal of the dilution at which 50% of the tubes show no such cytopathic effects.

The interferons produced by the above method are shown to be species specific using a plaque reduction interferon assay which involves incubation of an aliquot of the interferon-containing serum with individual cell cultures of various species followed by challenge with a virus, such as vesicular stomatitis virus or other known cytopathogenic virus, and incubation to alow virus plaque formation. Plaque numbers on interferon treated cultures are compared to those in untreated virus-infected control cultures. It is observed from such tests that interferon activity is demonstrated only in those cases wherein the cell cultures are of the same animal species as that from which the interferon-containing serum was isolated.

The interferons induced by the method of this feature of the present invention employing complexed polymers can be shown to be trypsin sensitive using a plaque reduction interferon assay, that is, the interferon activity is destroyed by trypsin treatment.

The interferon induced as hereinbefore described is further characterized by known methods as to isoelectric point and molecular weight as described in the examples.

The following discussion illustrates the preparation of the complexed polymers that are used in the method of this invention.

Preparation of Complexed Polymers

SUBSTANCE I: Preparation of a complex of Polyinosinic acid and Polycytidylic acid, "Poly (I:C)"

A solution of polyinosinic acid (I) is prepared which contains 550 μg/ml. in a buffer that is 0.01M glycylglycine and 0.1M sodium chloride. A solution of polycytidylic acid (C) is prepared containing 500 μg./ml. in the same buffer. The solution of polyinosinic acid and the solution of polycytidylic acid are then mixed to give a mole ratio of 1:1 with respect to the bases. The resulting solution is used directly as the source of the complexed polymers, "Poly (I:C)".

SUBSTANCE II: Preparation of a complex of Polyadenylic acid and Polyuridylic acid, "Poly (A:U)"

Using the procedure described above for preparation of Substance I, but employing equimolar amounts (with respect to bases) of polyadenylic acid (A) and polyuridylic acid (U) in place of the polyinosinic acid and polycytidylic acid used therein there is produced the complexed polymer, "Poly (A:U)."

SUBSTANCE III: Preparation of a complex of Polyinosinic acid and Cytidylylcytidine "Poly (I:CpC)"

By employing the procedure described above for preparation of Substance I, but substituting for the polycytidylic acid used therein an equimolar amount of cytidylylcytidine (CpC) an oligonucleotide, and using a buffer system composed of 0.006M sodium phosphate in 0.85% NaCl at pH 7.0 there is produced the complexed polymer, Poly (I:CpC).

Utilizing the method employed for the preparation of Substance I, but substituting for the polyinosinic acid and polycytidylic acid, equivalent amounts of other known homopolynucleotides, there is produced, for example, the following complexes, poly (A:I), poly (X:U), poly (A:8U), (G:C), poly (U:8A), wherein A, I, C, and U have the meanings assigned above, X represents polyxanthylic acid, G represents polyguanylic acid and 8A and 8U represent polyadenylic acid and polyuridylic acid respectively wherein each has 8 nucleotide units per polymer.

SUBSTANCE IV: Preparation of a complex of Polydeoxyinosinic acid and Polydeoxycytidylic acid, "Poly(dI:dC)"

Step A: Preparation of deoxyinosine-5'-triphosphate

Deoxyadenosine-5'-triphosphate (dATP) (200 μ moles, 126 mgs.) is dissolved in 24 ml. of water and cooled to 4° C. Sodium nitrite (9.6 gm) and 7.6 ml. of glacial acetic acid are added and the mixture left a 4° C. overnight. The reaction mixture then is diluted with 50 ml. of water and adjusted to pH 9 with 4M lithium hydroxide followed by 166 ml. of cold water. Clycine (2.8 ml. of 1M solution) (pH 9.2) and 8.4 ml. of 1M barium bromide then are added and the barium salt is precipitated with 286 ml. of cold ethanol. After standing at 4° C. for several hours, the salt is centrifuged down and washed several times with cold ethanol and dried over potassium hydroxide. The powder is suspended in 20 ml. of water and 1 ml. of 1N hydrochloric acid and then passed through a potassium-Dowex-50 column (a cation-exchange resin sold by J. T. Baker Co., Phillipsburg, N.J.) previously washed free of U.V.-absorbing material with water. The effluent from the column contains 160 $\mu$ moles of deoxyinosine-5'-triphosphate (dITP), and is stored frozen at $-20°$ C.

Step B: Preparation of Poly (dI:dC)

A reaction mixture for the synthesis of poly (dI:dC) contains 3.5 $\mu$ moles each of dITP and deoxycytidine-5'-triphosphate (dCTP), 600 $\mu$ moles of potassium phosphate buffer (pH 7.4) and 30 $\mu$ moles of magnesium chloride, and 40–80 units of DNA (deoxynucleic acid) polymerase in a total volume of 10 ml. After a lag period of 2–4 hours, polymerization is complete in 6–8 hours. The course of the reaction is followed by optical density measurements at intervals. When hypochromicity at 260 m$\mu$ is at a maximum, the reaction is stopped by adjusting the mixture to 0.2M sodium chloride and 0.1M sodium citrate. Dialysis is extensively carried out against the same buffer to remove all low molecular weight material. The product is stored frozen at $-20°$ C. until used for interferon induction.

The following examples are included to demonstrate the induction of interferon by the administration of certain of the homopolynucleotide complexes, such as those described above, both in living host animals and in isolated cell cultures and it should not be inferred therefrom that other complexed polymers contemplated by this invention though not exemplified will not stimulate interferon production in a like manner.

EXAMPLE 1

Induction of Interferon in Rabbits

The complexed polymers described above are separately administered as 0.5 ml. aliquots to 4.5 to 5.0 pound rabbits by intravenous injection. After about 2 hours, blood samples are taken from each rabbit by cardiac puncture. Serum is separated from each of the clotted blood samples and separately sterilized by exposure to ultraviolet irradiation. Aliquots of these sterilized samples are employed in the following tests.

Determination of Interferon Titers

The sterilized rabbit serum from each rabbit host is titrated separately by serial two-fold dilutions from 1:5–1:640 using cell culture growth medium as diluent. A one ml. sample of each dilution is added to each of four tube cultures of rabbit kidney cells which have been drained of spent growth medium. After overnight incubation at 35° C. the tube cultures are again drained and infected with 10 to 100 TCID$_{50}$ (Tissue culture infectious dose)$_{50}$ of Virus contained in 1 ml. of growth medium. Each tube culture is incubated at 35° C. for an additional 3 days, then observed for evidence of vital cytopathic effects and stored (+) for positive evidence of such effects or (0) for lack of evidence of cytopathic effects. The interferon titer for each serum sample is determined as the reciprocal of the serum dilution at which 50% of the tubes show no cytopathic effects. Serum from untreated animals (i.e., normal control animals) is titrated in each experiment to evaluate normal serum factors. The titers thus determined are shown in Table I.

TABLE I

Interferon Titers as Determined in Rabbit Kidney Tube Cell Cultures

| Polynucleotide | Dose/Animal | Interferon Titer |
|---|---|---|
| Poly I:C | 2 $\mu$g | >640 |
| " | 0.5 $\mu$g | 20–40 |
| " | 0.25 $\mu$g | <5 |
| Poly I only | 25 $\mu$g | <5 |
| Poly C only | 20 $\mu$g | <5 |
| Normal Controls | None | <5 |
| Poly A:U | 200 $\mu$g | 10–20 |
| " | 100 $\mu$g | 10–20 |
| " | 50 $\mu$g | 40–80 |
| " | 25 $\mu$g | 20–40 |
| " | 12.5 $\mu$g | 5–10 |
| " | 6.25 $\mu$g | 5–10 |
| Poly A only | 200 $\mu$g | <5 |
| Poly U only | 200 $\mu$g | 5 |
| Normal Control | None | <5 |
| Poly I:CpC | 100 $\mu$g | >640 |
| " | 10 $\mu$g | <5 |
| " | 1 $\mu$g | <5 |
| Poly CpC only | 50 $\mu$g | <5 |
| Normal Control | None | <5 |

Tests on rabbits given 1 $\mu$g of I:C in a single intravenous dose and then bled at successive intervals showed that a significant level of interferon appeared in one hour, reached a peak shortly thereafter, remained high for 4 to 6 hours and then declined.

EXAMPLE 2

Induction of Interferon in Mice

A solution of the poly (I:C) (Substance I), as well as solutions of polyinosinic acid and polycytidylic acid are separately administered as 0.2 ml. aliquots to 16–18 gram mice by intravenous injection. Each solution thus is administered to 25 mice. After about 2 hours, blood samples from each of the mice are taken. Serum is separated from each of the clotted blood samples. Sera from those animals that were injected with an aliquot of the same polynucleotide or complexed polymer solution are pooled and sterilized by exposure to ultraviolet irradiation, and titrated by the plaque reduction technique on mouse embryo cells against a vesicular stomatitis virus challenge. Pooled sera from untreated animals are similarly titrated.

TABLE II

Stimulation of Interferon Production in the Mouse as Assayed by Plaque Reduction Technique

| Complexed Polymer | Dose/Animal | Interferon Titer |
|---|---|---|
| Poly I | 55.0 $\mu$G. | <8 |
| Poly C | 50.0 $\mu$g. | <8 |
| Poly I:C | 52.5 $\mu$g. | 256 |
| Normal control buffered diluent | — | <8 |

EXAMPLE 3

Induced Resistance against Columbia SK Virus Infection of Mice

Columbia SK infection of mice results in symptoms of ruffled fur, lethargy, and flaccid paralysis followed by death in 3–5 days post-injection for the majority of animals. For evaluation of the effectiveness of the complexed polymers in inducing a protective amount of interferon, the following is the experimental procedure:

The test solution (0.5 ml.) of the complexed polymer of homopolynucleotide identified in Table III is administered intraperitoneally 18 hours pre-infection to each of 15 mice each weighing between 14-16 grams. Sufficient Columbia SK virus to kill 90% of mice by 5 days post-infection is injected subcutaneously in a 0.5 ml. aliquot and each mouse then is treated with 0.5 ml. of the test solution injected intraperitoneally 3 hours post-infection. Animals similarly treated with complexed polymer or homopolynucleotide but uninfected with virus are observed for evidence of toxicity produced by these chemicals. No evidence of toxicity is observed in any of the treated but uninfected animals. The animals continue their normal eating habits, continue to grow, and in all outward characteristics appear normal.

Daily accounts are kept of the number of live animals and the number of dead animals on that day. Animals are observed for 14 days.

TABLE III

Induced Resistance to Columbia SK Virus Infection of Mice

| Chemical Agent | Total mg. Dose per Animal | % Survival | Mean Survival Day |
|---|---|---|---|
| Phosphate buffer | — | 3.3 | 4.7 |
| Polyinosinic acid | 0.91 | 0.0 | 4.3 |
| Polycytidylic acid | 1.00 | 0.0 | 4.2 |
| Poly (I:C) | .525 | 53.3 | >14.0 |
| " | .263 | 60.0 | >14.0 |
| " | .131 | 53.3 | >14.0 |
| " | .065 | 46.7 | 13.0 |
| " | .033 | 33.3 | 8.0 |
| " | .017 | 40.2 | 7.0 |
| Controls | — | 2.2 | 5.0 |

When the same procedure is employed except that the post-infection dose is omitted, results comparable with those in Table III are obtained.

In another experiment in which separate groups of mice were given 525, 263 and 131 μg of I:C per mouse, the results showed a respective survival of 86%, 93% and 80% when challenged with the Columbia SK virus. I and C alone at 550 μg. and 500 μg dose, respectively were inactive.

EXAMPLE 4

Induced Resistance against Pneumonia Virus (PVM) Infection of Mice

Pneumonia virus of mice (PVM) infection of mice by intranasal inoculation results in a respiratory virus infection culminating in pneumonia with death occurring 6-7 days post-infection for the majority of animals.

Solutions of complexed polymers and of homopolynucleotides are tested for capacity to protect against PVM infection by pretreating twenty 8-10 gram mice intranasally with 0.03 ml. of the solution containing test material in Table IV 4 hours before intranasal inoculation with virus. Sufficient virus is used to kill 75% of the mouse population by 6-7 days post-inoculation. By completion of the experiment (14 days), 59 of the 60 infected by untreated mice had died of virus infection.

Daily records are kept of the number of live animals and the number of dead animals on that day. Animals are observed for 14 days.

TABLE IV

Induced Resistance to Infection of Mice with Pneumonia Virus of Mice (Intranasal)

| Chemical Agent | Dose in μg. per mouse | % Survival | Mean Survival Day |
|---|---|---|---|
| poly (I:C) | 15.75 | 100 | >14.0 |
| " | 8 | 95 | >14.0 |
| " | 4 | 95 | >14.0 |
| " | 2 | 82 | >14.0 |
| " | 1 | 80 | >14.0 |
| " | 0.5 | 47.3 | 12.0 |
| " | 0.25 | 40 | 11.0 |
| " | 0.13 | 5.3 | 8.0 |
| " | 0.06 | 5.0 | 8.0 |
| " | 0.03 | 2.2 | 8.0 |
| Phosphate Buffer | — | 0.0 | 7.0 |

EXAMPLE 5

In Vitro Activity of Complexed Polymers as Viral Inhibiting Substances

To determine the kinetics of interferon induction by I:C in an in vitro system, I:C was added in the amount of 10 μg/ml. to trypsinized spleen cells from 6 week old rabbits suspended in Eagle's spinner culture medium containing 10% agamma calf serum. Periodic assay for interferon production showed a gradual increase up to 7.5 hours and a same quantitative amount at 19 hours.

To determine the effectiveness of the complexed polymers in various cell cultures each of the cell cultures identified in Table V is incubated overnight with one of the complexed polymers diluted in the growth medium known to be required by the cell culture used. After removal of the growth medium containing the complexed polymers each culture is infected with vesicular stomatitis virus suspensions, incubated, and observed for plaque formation described for the test demonstrating species specificity.

TABLE V

μg. Dose of Complexed Polymer/ml. required to Induce Resistance to VSV Plaque Formation

| Cell Culture | Poly I:C | Poly A:U |
|---|---|---|
| Primary Rabbit Kidney | <0.00125 | 0.0015 |
| Primary Human Amnion | 0.04 | 26.25 |
| Primary Human Embryonic Kidney | 1.25 | |
| Primary Chick Embryo | 0.33 | >100 |
| Primary Bovine Kidney | 5.00 | — |
| Primary Dog Kidney | 1.25 | — |
| Primary Mouse Embryo | >5.25 | >100 |

The relative effects of the complexed polymers and of their separate components is shown in Table VI.

TABLE VI

Concentration of Complexed Polymer Required to Induce Resistance to VSV Plaque Formation on Primary Rabbit Kidney Cell

| Polymer | μg/ml |
|---|---|
| Poly I | >11 |
| Poly C | >10 |
| Poly I:C | <0.00125 |
| Poly A | >11 |
| Poly U | >10 |
| Poly A:U | 0.0015 |

Utilizing the method described in Examples 1-5 but substituting Substance IV or the complexed polymers disclosed after the description of Substance III, for Substances I, II and III used therein, similar results are obtained.

The interferons are identified as relatively low molecular weight protein molecules possessing the capacity to interfere with viral replication only in cells of the same species from which the interferons were produced. Characterization of inteferons has employed demonstration of species specific, antiviral activity, trypsin sensitivity (a test for proteins), isoelectric point, and molecular weight determinations.

The following tests serve to so identify the active viral inhibiting substances as interferons.

Demonstration of Species Specificity of the Induced Interferon

Samples (3 ml.) of 2-fold serial dilutions in culture medium of the interferon samples from Example 1 sterilized by exposure to ultraviolet irradiation are added to monolayers of various types of cells grown separately in 30 ml. tissue culture flasks. After overnight incubation, the serum samples are drained off and replaced by 0.5 ml. of vesicular stomatitis virus suspension and the cultures reincubated at 35° C. for an additional 1.5 hours. An overlay of 5 ml. of maintenance culture medium containing methylcellulose as a solidifying agent is added to each flask and incubation continued for an additional 3–4 days at 35° C. to allow virus plaque formation. The overlay medium then is removed and the cells stained with carbol fuchsin. Plaque numbers on interferon treated monolayers are compared to those in untreated virus infected control monolayers. The reciprocal dilution of inferferon giving at least a 50% reduction in plaque number is considered the interferon titer of that sample. The titers thus determined illustrate species specificity, that is, interferon induced in an animal of a given species is active only in cells derived from an animal of that same species. These titers are shown in Table VII.

TABLE VII

Species Specificity of Induced Interferons in Tests with Vesicular Stomatitis Virus Challenge

| Complexed Polymer | Source of Serum | Interferon titer assayed on cell culture | | | |
|---|---|---|---|---|---|
| | | Chick Embryo | Mouse Embryo | Rabbit Kidney | BSC* Monkey |
| I:C | Rabbit | — | <16 | >2048 | 21 16 |
| I:C | Mouse | <8 | 128 | <16 | — |
| A:U | Rabbit | <32 | <8 | 512 | — |
| I:CpC | Rabbit | — | <8 | >2048 | — |
| Untreated | Rabbit | — | <16 | <16 | <16 |

*BSC
an established cell line derived from African green monkey kidney cells

Demonstration of Trypsin Sensitivity of Induced Interferon

Interferon-containing serum from animals induced with a complexed polymer is isolated by chromatography on CM-Sephadex (a cation-exchange material obtained by the introduction of carboxymethyl groups into Sephadex). A sample of the isolated interferon is treated with crystalline trypsin solution (50 µg./ml. final concentration) for 4 hours at 35° C. A similar untreated interferon sample is also incubated for 4 hours at 35° C. After the 4 hour incubation period, soybean trypsin inhibitor is added to each sample, including the control. The samples are titrated for interferon activity by the plaque reduction method. Trypsin solution to which soybean trypsin inhibitor has been added is also titrated for antiviral activity. The results of the trypsin sensitivity test are given in Table VIII.

TABLE VIII

Trypsin Sensitivity of Induced Interferon

| Treatment | Interferon Titer |
|---|---|
| Poly (I:C) induced interferon + trypsin | 16 |
| Poly (I:C) induced interferon | 256 |
| Trypsin control | 16 |
| Poly (I:CpC) induced interferon + trypsin | 8 |
| Poly (I:CpC) induced interferon | 1024 |
| Trypsin control | <8 |

Determination of Molecular Weight of Induced Interferon

The molecular weights of complexed polymer induced inteferon are determined according to the following method. Columns of 2 × 35 cm. size are packed with hydrated Sephadex G-200 beads and slowly percolated for 2 to 3 days with 0.006M sodium phosphate-0.15M NaCl, pH 7 buffer to achieve equilibrium (Sephadex is a hydrophilic insoluble substance formed by cross-linking the polysaccharide dextran. The designation "G-200" refers to the degree of cross-linking and, therefore, the porosity of the hydrated gel). One milliliter amounts of the serum containing induced interferon prepared as described in Example 1 is applied to the columns. The flow rate in the column is adjusted to 20–25 ml. per hour and fractions are collected in 3 ml. amounts. The fractions are assayed for interferon content by the plaque reduction method and the molecular weight of each sample is calculated according to the formula $M^{\frac{1}{3}} = 146 \, [1.480\text{-}V/Vo^{\frac{1}{3}}]$ in which "M" is the molecular weight, "V" is the elution volume of the material tested and "Vo" is the void volume of the column. This method yields values within 10% of reported molecular weights when tested with purified proteins.

The results of the molecular weight determinations are as follows:

| Rabbit Interferon | Molecular Weight |
|---|---|
| Poly (I:C) Induced | 49,000–52,000 |

Determination of Isoelectric Point of Interferon

The serum samples containing interferon prepared as described in Example 1 are dialyzed overnight against 0.1M sodium phosphate buffer, pH 6.0, or simply diluted 1:3 with buffer. Twenty milliliters of each sample is applied to a 1.5 × 10 cm. CM-Sephadex column equilibrated with the same buffer and the interferon is eluted by successive addition of 5 ml. amounts of 0.1M sodium phosphate with increasing increment of 0.2 pH unit. The effluent is collected in 5 ml. fractions and the pH and inteferon activity of each is measured. The pH of the fraction with peak activity is noted and the isoelectric point is calculated by adding a 0.4 pH unit. The isoelectric point thus determined for interferons induced in the rabbit by the administration of Poly (I:C) is 6.8 to 6.9.

The above description concerning the preparation of the complexed polymers and the examples illustrating the method of this invention specifically describe certain aspects of this invention. It is not to be considered limiting as the invented method can be carried out with complexed polymers made from known homopolynucleotides, homooligonucleotides or their deoxy analogs administered parenterally or topically as hereinbefore described. Moreover, the invention includes the formation of the complexed polymers in the host cell, or animal or person, after the concomitant administration to the host of the two homopolynucleotides selected to form the polymer. Thus, the two homopolynucleotides may jointly be sprayed on the oral-nasal membranes or be administered intraparenteral or intravenously. Support for this resides in the fact that 26 $\mu$g. of a simple mixture of poly I and poly C in distilled water induced interferon on injection in rabbits, thus indicating that the complex I:C took place in the rabbit blood.

Physical and Chemical Properties of I:C Complex Polymers

Mention has been made above to the hypochromic shift in the UV spectrum which results when the complexed polymer is formed from its monomers. Other evidence of I:C formation and the prevention of its complexing has been found and this evidence applies as well to the other complex polymers used in this invention. That I and C polymers complexed readily is shown by a marked hypochromic effect when compared with a mixture of poly I and poly C which is prevented from complexing. Thus if poly C is treated with 0.4% formaldehyde so that it cannot complex when mixed with poly I, a UV absorption spectrum results which is the sum of the spectra of uncomplexed poly I and poly C. A similar solution of the I:C complex polymers shows a marked decrease in the optical density of the solution in the 240-260 m$\mu$ range. Thus the amino groups of the C were bound by prior treatment with 0.4% formaldehyde (C—HCHO), the mixed polynucleotides were no longer capable of hydrogen bonding and gave an ultraviolet absorption spectrum which was equal to the summation of the individual absorptions of the two polynucleotides. Whereas 26 $\mu$g of I:C readily induced interferon in rabbits, 26 $\mu$g of I + C-HCHO solution did not induce interferon.

Deamination of C was carried out with 0.1M sodium nitrate at pH 4.0 for 1 hour at 0° C. Excess nitrous acid was quenched by addition of urea and low molecular weight products were removed by dialysis. The I + deaminated C mixture was inactive at 26 $\mu$g in interferon induction.

Prior treatment of the C(50 $\mu$g/ml) with bovine pancreatic RNase (1 $\mu$g/ml) for 4 hours at 25° C. effected a degradation of the C to shorter chain lengths as evidenced by increase in optical density during incubation. The RNase-degraded C did not interact with I as evidenced by lack of hypochromicity and the solution (26 $\mu$g) was inactive as an interferon inducer.

The existence of the I:C complex is shown by its degradation by RNase. To show this I:C at 40 $\mu$g/ml was incubated in a quartz cuvette at 25° C. with bovine pancreatic RNase (0.4 $\mu$g/ml) at pH 7.0 and the resulting degradation of the complex was followed by measuring the change in optical density with a recording spectrophotometer equipped with a controlled heater compartment. A marked increase in the optical density, particularly in the 220-260 m$\mu$ range shows that I:C was degraded by RNase. Under the same conditions, double-stranded RNA from type 3 reovirus virions was not appreciably affected. The RNase degraded I:C had reduced capacity to induce interferon in rabbits.

The existence of the I:C complex is also shown by its pH sensitivity. To show this I (27.5 $\mu$g/ml), C (24.0 $\mu$g/ml), and I:C (52.5 $\mu$g/ml) in phosphate buffered saline, pH 7.0, were titrated with increments of alkali. An increase in alkalinity from pH 7 to pH 10.8 showed that an abrupt hyperchromic effect at pH 9.5-10.0 occurred from I:C, but not for I and C alone. Unlike the absorption spectrum at neutral pH, the absorption spectrum of I + C solution at pH 10.8 was identical to that calculated from the uncomplexed I and C at pH 10.8. Thus, at pH 9.5-10.0 the I:C underwent dissociation to form a solution of uncomplexed I and C.

Mixtures of I and C at the same concentrations but at pH 7.5, and 10.8 were titrated for interferon induction in rabbits. The material at pH 7.5 gave interferon induction at 0.33 $\mu$g while that at 10.8 required 1.31 $\mu$g to give induction in the rabbit. This was interpreted to indicate that complexing of I and C did take place in the environment of the rabbit bloodstream but to a lesser degree than when the 2 substances were premixed at optimal pH. This interpretation was supported by the demonstration that I and C did not detectably form a complex in distilled water. Yet 26 $\mu$g of the mixed polynucleotides in distilled water induced interferon in rabbits, suggesting that complexing did take place in the rabbit blood.

(B) NUCLEIC ACID FROM P. FUNICULOSUM

The present invention also involves the discovery that a certain double-stranded ribonucleic acid (hereinafter called HeI-RNA) can be isolated from a known fungus grown under artificial conditions and can be used as an inducer to cause the production of exceptionally large amounts of interferon. This particular nucleic acid is one of the many which occurs in the mycelium of *P. funiculosum* under these synthetic growth conditions and its isolation and recovery in purified form is a feature of this invention. It is believed that this nucleic acid has not been known or identified prior to the present invention and in fact, it is entirely possible that the methods for its isolation and recovery result in its chemical conversion from the inactive form in which it is produced by the fungus during its controlled growth.

The mold *P. funiculosum* is known as its characteristics are described in commonly available text books. It is available from various type culture collections such as those maintained in the A.T.T.C. and Regional Laboratories. It appears that all species conforming to the general description for this species will be producers of the nucleic acid which is the feature of this invention.

In general, this fungus is grown in a conventional nutrient culture medium known to support the growth of molds, the mycelium is collected and subjected to isolation steps to recover the nucleic acid of this invention, and this nucleic acid is employed as the inducer to cause an augmented production in host cells of interferon.

The nucleic acid of this invention was produced, isolated and purified as set forth in the following representative example:

(a) A conventional culture medium known to be suitable to support the growth of molds or fungus may be used for growing *P. funiculosum*. A representative culture medium contained the following agents per liter: 66.6 gm dextrose, 3.3 gm NaNO$_3$, 16.2 gm yeast autolysate, 1.1 gm K$_2$HPO$_4$, 0.55 gm MgSO$_4$.7H$_2$O, 0.55 gm KCl, 0.011 gm Rochelle salts, 0.011 gm FeSO$_4$.7H$_2$O, 0.0011 gm ZnSO$_4$.7H$_2$O, preferably but not essentially a defoamer, and water to make up a total of one liter. The culture was incubated for 72 hours at 26° C. with continuous aeration and agitation. This fermentation was monitored for pH change, dextrose utilization, and mycelium production. One hundred gallons of this fermentation broth was filtered and the residual mycelium cake (36 pounds) was recovered.

(b) This cake was combined with a slightly alkaline phosphate buffer, i.e. between pH 7.5 and 9.0. For example the mycelium cake was suspended in pH 8.0 phosphate buffer (33 gallons) and stirred vigorously at room temperature for one hour. The buffer mixture was prepared as follows:

| 20 liters pH 8.0 phosphate buffer | | |
|---|---|---|
| $Na_2HPO_4$ | 92.58 g | dilute to 20 liters |
| $NaH_2PO_4$ | 5.52 g | |

The mycelium cake suspension was filtered and the clear filtrate or extract was retained (31 gallons.)

(c) To the clear filtrate is added about an equal amount of a water-miscible organic solvent known to cause the precipitation of proteins such as acetone, methanol and ethanol. In the example, there are added slowly to the mycelium extract with stirring 28 gallons of acetone. The mixture was allowed to stand overnight at room temperature to allow the precipitation of the solids which formed and the soluble portion was carefully decanted away from the insoluble fraction.

(d) The precipitate was then centrifuged at 6500 rpm for 30 minutes, the supernatant liquid then being discarded.

(e) The precipitate was then combined with enough water to assure extraction of the nucleic acid complex. In the example, 2.5 liters of water was used. The water extract was then centrifuged clear, and the insoluble portion discarded.

(f) The clear aqueous extract was then dialyzed in 30/32 dialysis casing against 10 gallons of distilled water for 24 hours at 4° C., to assure removal of dialyzable materials. It may be dialyzed an additional 24 hours with a change of water.

(g) The non-dialyzable fraction (retentate) was centrifuged at 6500 rpm and the clear soluble portion was concentrated 25-fold by centrifugation 18 hours at 35,000 × G to obtain a pellet, which is recovered.

(h) The 25-fold concentrate is suspended in a neutral, dilute sodium phosphate buffer, such as a 0.01M sodium phosphate at pH 7.

(i) This is clarified by centrifuging for 10 minutes at 2000 rpm, the supernatant being recovered.

(j) A phenol extraction using 88% liquified phenol was then carried out at 35°–40° C. for 30 minutes, using about an equal volume of the phenol. The phenol treatment is believed to break up the complex in which the nucleic acid of the invention is bound.

(k) The mixture was centrifuged at 2000 rpm for 30 minutes at 5° C. to separate the aqueous from the phenol layer and the phenol was discarded.

(l and m) The phenol extraction and centrifugation was carried out twice more at room temperature for 30 minutes each.

(n) The aqueous layer was dialyzed against a large volume (50–100 volumes) of 0.01M sodium phosphate pH 7 buffer to remove residual phenol.

(o) Further purification was obtained by chromatography on Ecteola cellulose [the synthesis of this material was described by Peterson et al in 78 JACS, 751–756, (1956)] which removed a large amount of inactive polysaccharide remaining after the phenol extraction.

A column 1.5 × 10 cm of Ecteola cellulose was prepared by suspending the ion-exchange material, successively in 0.5N NaOH, distilled water, 0.5M $NaH_2PO_4$, and then in 0.01M sodium phosphate having a pH 7. This last slurry was poured into a glass column and washed through with about 200 ml. of 0.01M sodium phosphate, pH 7, buffer. About 100–120 ml. of the dialyzed, phenol extracted 25-fold concentrate was applied to the column.

(p) The column was eluted with a stepwise NaCl gradient from 0.1M to 0.5M in 0.05M steps as this removed the impurities.

(q) It was then eluted stepwise from 0.5M to 0.8M in 0.1M steps, each step being 20 ml. The NaCl gradient was collected in 20 ml. fractions in both cases. The interferon inducing activity peak was contained in the fractions following both the 0.5 and 0.6M NaCl additions.

Rechromatography. The peak fractions of activity eluted from the 0.5 and 0.6M NaCl steps were pooled and dialyzed against 0.01M sodium phosphate, pH 7. Of this once chromatographed material, 100 ml. was applied to a column of Ecteola cellulose 1.5 × 6 cm. Chromatography was performed under conditions identical to the first chromatography. The interferon inducing activity was again eluted in the 0.5M and 0.6M NaCl additions. All but a trace amount of inactive polysaccharide was eliminated during the second chromatography.

PRESENCE OF AN INHIBITOR OF THE INTERFERON INDUCER IN CRUDE EXTRACTS

The importance of the phenol addition step in releasing or otherwise making available the RNA of the invention is shown by the following: The increase in the inducing capacity of crude extracts which had been concentrated by centrifugation, on dilution or following phenol extraction strongly suggests the presence of a protein inhibitor which partially or completely masks the presence of the interferon inducer in various batches. The following data demonstrate this:

| Activation of interferon inducer by phenol extraction | | |
|---|---|---|
| Inducer | Dilution | Average Interferon Titer* |
| Concentrated P. funiculosum extract | 1:2 | 5 |
| " | 1:4 | 40 |
| " | 1:8 | 40 |
| " | 1:16 | 5 |
| Concentrated P. funiculosum extract after phenol treatment | 1:2 | 640 |
| " | 1:4 | >640 |
| " | 1:8 | 160 |
| " | 1:16 | 40 |
| Normal | | 5 |

*Interferon induced in rabbits as explained in Example 1.

PROPERTIES OF THE NUCLEIC ACID

The purified inducer of interferon was characterized as a ribonucleic acid (RNA) by the following criteria: (1) ultraviolet spectrum typical of a nucleic acid, e.g. maxima at 257.5 and minima at 230 millimicrons, max./min., density ratio of 0.72/0.31 = 2.30 and 260/280 density ratio of 0.72/0.33 = 2.18, (2) a reduction in interferon inducing activity following incubation at 37° C. to 56° C. temperatures with ribonuclease, (3) resistance to deoxyribonuclease, sodium periodate and formalin, (4) presence, shown by chemical analysis, of constituents normally found in RNA, (5) other chemical analyses and (6) thermal decomposition. These are illustrated as follows:

(1) Ultraviolet adsorbtion spectrum.

The ultraviolet adsorption spectrum is determined in a Beckman DU or DB-G spectrophotometer and is similar to known nucleic acids from various sources.

(2) Demonstration of Ribonuclease sensitivity of the Interferon Inducer.

The purified interferon inducing agent isolated from *P. funiculosum* was incubated and at each temperature an additional sample contained added pancreatic ribonuclease (chromatographically pure). The incubated ribonuclease treated and untreated samples were tested for induction of interferon in rabbits; the results are presented in Table IX.

TABLE IX

Demonstration of Ribonuclease sensitivity of the Interferon Inducer

| Ribonuclease Concentration | Temp. of Incubation | Time of Incubation | Interferon Titer |
|---|---|---|---|
| — | 25° C | 30 min. | 320, 640 |
| 0.2 µg/ml | 25° C | 30 min. | 320 |
| — | 37° C | 2 hrs. | 320, 640 |
| 2.0 µg/ml | 37° C | 2 hrs. | <5 |
| — | 56° C | 2 hrs. | 640 |
| 2.0 µg/ml | 56° C | 2 hrs. | <5 |

Table IX shows that the HeI-RNA is quite insensitive to degradation by RNase at 0.2 µg/ml when incubated at 25° C. for 30 minutes. This stability is also shown by a measurement of the percent increase in optical density measured at 260mµ. Under the conditions of Table IX the comparative increase in optical density of previously denatured HeI-RNA and yeast RNA is shown in the following Tables X and XI.

TABLE X

Increase in Optical Density due to Degradation of 20 µg/ml RNA Solution using 0.2 µg/ml Pancreatic RNase at 25° C and pH 7.

| Substance | Time in Min. | Increase in Optical Density at 260 mµ in % |
|---|---|---|
| Undenatured HeI-RNA | 0 | 0 |
| " | 10 | 0 |
| " | 20 | <1 |
| " | 30 | <1 |
| Denatured HeI-RNA | 0 | 0 |
| " | 10 | 10 |
| " | 20 | 11 |
| " | 30 | 12 |
| Yeast RNA | 0 | 0 |
| " | 10 | 12 |
| " | 20 | 15 |
| " | 30 | 16 |

TABLE XI

Increase in Optical Density due to Degradation of 20 µg/ml RNA Solution using 10µg/ml Pancreatic RNase at 56° C and pH 7.

| Substance | Time in Min. | Increase in Optical Density at 260 mµ in % |
|---|---|---|
| Undenatured HeI-RNA | 0 | 0 |
| " | 40 | 3 |
| " | 80 | 6 |
| " | 120 | 8.5 |
| Yeast RNA | 0 | 0 |
| " | 40 | 12.5 |

TABLE XI-continued

Increase in Optical Density due to Degradation of 20 µg/ml RNA Solution using 10µg/ml Pancreatic RNase at 56° C and pH 7.

| Substance | Time in Min. | Increase in Optical Density at 260 mµ in % |
|---|---|---|
| " | 80 | 14 |
| " | 120 | 14 |

(3) Demonstration of Lack of Deoxyribonuclease, Formalin and Periodate Sensitivity A solution containing 16 µg of the purified HeI-RNA per ml. was adjusted to pH 6 and sodium periodate was added and at the end of the test the excess periodate was destroyed by the addition of 1% glycerol. This was followed by dialysis against phosphate buffered saline. Another like solution of the interferon inducer was incubated with electrophoretically purified deoxyribonuclease. Still another like solution of the HeI-RNA was incubated with formalin. The above treated solutions were tested for induction of interferon in rabbits; the results are presented in Table XII.

TABLE XII

Demonstration of Lack of Periodate, Formalin Deoxyribonuclease Sensitivity of the Inducer

| Treatment Substance | Concentration | Temp. °C | Time | Interferon Titer |
|---|---|---|---|---|
| — | — | 25 | 1 hr. | 40–320 |
| Na. Periodate | 0.01M | 25 | 1 hr. | 40–640 |
| — | — | 25 | 1 hr. | 40–320 |
| Deoxyribonuclease | 5 µg/ml | 25 | 1 hr. | 40–640 |
| — | — | 35 | 4 hrs. | 320–640 |
| Formalin | 1.5% | 35 | 4 hrs. | 640 |

Table XII shows that HeI-RNA is quite insensitive to formalin. This is also shown a comparative analysis of the optical density of a 20 µg/ml solution of the HeI-RNA before and after incubation with 1.5% formaldehyde for 4 hours at 35° C. Such a test shows no significant change in optical density when measured at 260 mµ. A similar analysis using yeast ribosomal RNA showed an increase in optical density at 260 mµ from 0.5 to 0.6. It also showed a shift in the absorbancy maximum from 255 to 260 mµ. This may be taken as an indication of the presence of fewer free amino groups in the HeI-RNA than in the yeast RNA and the presence of a double-stranded helix.

(4) Determination of Chemical Analysis of the Base Composition of the Interferon Inducer The base (purine and pyrimidine) composition was determined by hydrolyzing a dried sample of the interferon inducer with 12N perchloric acid for two hours at 100°. The acid hydrolysate was chromatographed on Whatman Number 1 filter paper along with the four bases (adenine, guanine, cytosine, and uracil) normally found in ribonucleic acids. The bases are located as spots on the paper by means of ultraviolet light, cut out and eluted with 0.1N hydrochloric acid. From the Rf values (distance of base from origin divided by distance traveled by the solvent) the identity of the ultraviolet light adsorbing spots on the filter paper are determined. From the absorption spectrum of the eluted spots identification of the bases found in the interferon inducer acid hydrolysate are determined; the results are presented in Table XIII.

TABLE XIII

| Base Composition of the Interferon Inducer | | |
|---|---|---|
| Base Identified | Rf | Rf (lit.ref.) |
| Adenine | 0.24 | 0.25 |
| Guanine | 0.34 | 0.36 |
| Cytosine | 0.46 | 0.47 |
| Uracil | 0.66 | 0.68 |

Solvent system used in paper chromatograph of the purine and pyrimidine bases was isopropanol-HCl-water. Lit. Ref.Fink, K., and Adams, W., J. of Chromatography 22 (1966), p. 118.

(5) Other Chemical Analyses of Interperon Inducer

TABLE XIV

| Chemical Component | % Found | % Theory |
|---|---|---|
| Ribose | 38.0 | 36.5 |
| Phosphorus | 8.4 | 8.6 |
| Protein | <1 | — |
| Polysaccharide | <1 | — |
| Deoxyribose | None | — |

(6) Sedimentation Analysis

The sedimentation coefficient ($S_{20,W}$) was determined and found to have an average value of 12.1.

(7) Thermal Denaturation

Thermal denaturation of HeI-RNA was measured in experiments performed using a Beckman DB-G spectrophotometer equipped with a Tm analyzer and recorder to measure temperature and optical density at 260 m$\mu$. The increase in absorbancy of the double-stranded HeI-RNA at 260 m$\mu$ was shown to be a function of temperature at two different salt concentrations. In SSC (0.15 M NaCl - 0.015 M sodium citrate, pH 7.0, there was only small increase in absorbancy i.e. about 8%, even at 100° C. indicating that the Tm (Thermal transition midpoint) was higher than this figure. At the lower ionic strength (0.1 SSC) hyperchromicity of 32% occurred principally in the range of 85° to 100° C. with a Tm of 95° C. Singlestranded RNA from yeast ribosomes showed lesser hyperchromicity (20%) and this was over a broad temperature range between 40° and 75° C. (Tm 55° C.) in SSC. These findings showed that HeI-RNA has a high level of thermal stability. When the HeI-RNA in SSC was heated with formaldehyde in a concentration of 2.76% it resulted in a 44% increase in absorbancy of HeI-RNA in SSC on heating to 95° C. Haselkorn and Doty have demonstrated that formaldehyde reduces the Tm of hydrogenbonded helical polynucleotides.

The following examples illustrate the use of the RNA of this invention as an inducer of interferon production.

EXAMPLE 6

Induction of Interferon in Rabbits

The purified RNA fraction from *P. funiculosum* is administered to rabbits by intravenous injection as explained above with the I:C complexed polymers. The titers thus determined are shown in Table XV.

TABLE XV

| Interferon Titers as determined in Rabbit Kidney Tube Cell Cultures | |
|---|---|
| Dose per animal | Interferon Titer of Serum |
| 8 $\mu$g | 80 - >640 |
| 2 $\mu$g | 80 - 160 |
| 0.125 $\mu$g | 5 - 10 |

TABLE XV-continued

| Interferon Titers as determined in Rabbit Kidney Tube Cell Cultures | |
|---|---|
| Dose per animal | Interferon Titer of Serum |
| none | <5 |

As explained above, the interferon so produced in vivo can be isolated and be characterized by the known described methods. This includes:

(a) Demonstration of Species Specificity of the Induced Interferon

The titers thus determined from using HeI-RNA illustrate species specificity, that is, interferon induced in an animal of a given species is active only in cells derived from an animal of that species. These titers are shown in Table XVI.

TABLE XVI

| Species Specificity of Induced Interferon in Tests with Vesicular Stomatitis Virus Challenge | | | | |
|---|---|---|---|---|
| | | Interferon titer assayed on cell culture | | |
| Exp. No. | Source of Serum | Chick Embryo | Mouse Embryo | Rabbit Kidney |
| 1 | Rabbit | — | <20 | 160 |
| 2 | Rabbit | <6 | <12 | 96 |

(b) Demonstration of Trypsin Sensitivity of Induced Interferon

Interferon-containing serum from animals induced with purified RNA fraction from *P. funiculosum* is isolated as explained above and the results of the trypsin sensitivity test are given in Table XVII.

TABLE XVII

| Trypsin Sensitivity of Induced Interferon | |
|---|---|
| | Interferon Titer |
| Interferon alone | 52 |
| Interferon plus Trypsin | <20 |
| Trypsin Control | <20 |

(c) Determination of Molecular Weight of Induced Interferon

The molecular weight of *P. funiculosum* RNA induced interferons is determined according to the above described method. This method yields values within 10% of reported molecular weights when tested with purified proteins.

The results of the molecular weight determination are as follows:

TABLE XVIII

| Rabbit Interferons | Molecular Weights |
|---|---|
| P. Funiculosum RNA Induced | 60,000 and 130,000 |

(d) Determination of Isoelectric Point of Interferon

The serum samples containing interferon induced by the HeI-RNA are analyzed as explained above. The isoelectric point thus determined for interferon induced in rabbit serum by the administration of *P. funiculosum* RNA is 6.9–7.1.

EXAMPLE 7

Induced Resistance against Columbia SK Virus Infection of Mice

The experimental procedure explained above was used. Animals similarly treated with *P. funiculosum* RNA but uninfected with virus are observed for evidence of toxicity produced by this chemical. No toxicity is observed in any of the treated but uninfected animals. The animals continue their normal eating habits, continue to grow, and in all outward characteristics appear normal.

Daily accounts are kept of the number of live animals and the number of dead animals on that day. Animals are observed for 10 days. The results are presented in Table XIX.

TABLE XIX

Induced Resistance against Columbia SK Virus Infection Of Mice

| Chemical Agent | Total Dose Per Animal | % Survival | Mean Survival Day |
|---|---|---|---|
| P. funiculosum RNA | 50 μg* | 73.3 | 12.0 |
| Phosphate buffer | — | 0.0 | 3.1 |

*Sample contained 50 μg. RNA/ml. 0.5 ml. was administered 18 hours prior to virus challenge and 0.5 ml. was administered 3 hours after virus challenge.

EXAMPLE 8

Induced Resistance against Pneumonia Virus (PVM) Infection of Mice

Solutions of the purified RNA are tested for ability to protect against PVM infection by the method described above. The results are presented in Table XX.

TABLE XX

Induced Resistance to Infection of Mice with Pneumonia Virus of Mice

| Chemical Agent | Total Dose Per Animal | % Survival | Mean Survival Day |
|---|---|---|---|
| P. Funiculosum RNA | 20 μg. in 0.03 ml. | 90.0 | >14 |
| Phosphate buffered saline | 0.03 | 0 | 7 |

(C) RIBONUCLEIC ACID FROM REOVIRUS TYPE 3 VIRIONS

As a further feature of this invention, an RNA obtained from reovirus type 3 virions and which is doublestranded is an excellent stimulator of interferon production. This RNA is hereinafter referred to as Reo 3-RNA.

To obtain this Reo 3-RNA, Dearing strain reovirus type 3 was grown in primary cell cultures of grivet monkey kidney according to conventional practices and harvested after 3–4 days incubation at 35° C. The reovirus type B virions in the cell culture fluid was concentrated 50-fold by the acid precipitation method described by Charney, et al: Charney, J., R. Machlowitz, A. Tytell, J. Sagin, and D. S. Spicer, Virology, 15 269 (1961).

The precipitate was collected and resuspended in sodium phosphate buffer, pH 8, equivalent to a 50-fold concentrate of the original virus pool and was clarified by centrifuging for 10 minutes at 3,000 rpm (or 15 minutes at 1,500 rpm). The supernate was then centrifuged at 78,000 × g for 3 hours. The pellet which contained the virus was resuspended in sodium phosphate-buffered saline, pH 7.0 containing 0.005 M magnesium chloride to give a 500-fold concentrate of starting material.

Further purification of the virus and extraction and purification of the Reo 3-RNA was by the procedure of Gomatos and Tamm, mentioned above.

This RNA was noninfectious based on tests for infectivity in susceptible monkey renal cells and in L cells. The lack of infectivity of such RNA has been repeatedly shown, such as by Gomatos, et al; Gomatos, P. J., and W. Stoeckenius, Proc. Natl. Acad. Sci., 52, 1449 (1964).

Gomatos and Tamm, mentioned above, described the ribosonucleic acid of reovirus as a double-stranded molecule and tests such as described above, carried out on this RNA, confirm this fact. Data obtained by us on interferon induction in animals by this reovirus RNA support the feature of this invention that double-stranding is a requisite of RNA for interferon induction activity.

This Reo 3-RNA was highly active on intravenous injection in inducing interferon in rabbits employing as little as 0.5 μg dose of RNA per rabbit. A high level of interferon appeared within 1 hour after injection of 8 μg per 0.5 ml. dose (the amount obtained from $8 \times 10^{10}$ virions); the Reo 3-RNA, reached a peak by 2 hours, and declined slowly to less than 1/16 the peak level 4 hours later. Infectious reovirus type 3 virions at the quivalent dose level did not induce a significant amount of interferon before 5 hours and the maximum level was no more than 1/16 that induced by RNA. This suggests that the whole virus does not become effective as an interferon inducer until double-stranded RNA has been released, i.e., that time is required for viral uncoating of the whole virus. It is worthy of note, also, that the naked RNA was far more efficient as an inducer than was the whole virus. The short induction period shown by the Reo 3-RNA corresponds to that for induction by the complexed synthetic polynucleotides discussed above.

Identification of the viral inhibitory substance in the sera of rabbits injected with Reo 3-RNA was based on the biological and biochemical properties which have been referred to above. These are: (a) Host species specificity showing inhibitory titers of 128–256 in homologous rabbit kidney cells and <32 in heterologous mouse embryo and chick embryo cells in culture; (b) reduction in titer from 32 to <2 by treatment for 4 hours at 35° C. with 50 μg/ml trypsin; (c) molecular weight of 40,000 based on Sephadex G-200 gel filtration; and (d) isoelectric point 7.0 measured by chromatography on CM-Sephadex.

Tests performed in monolayer primary cell cultures of rabbit kidney carried out as described above showed that <0.04 μg of Reo 3-RNA were required to prevent formation of plaques by vesicular stomatitis virus.

The ultraviolet absorption spectrum of Reo 3-RNA was typical for nucleic acid with minimum at 232 and maximum at 260 mμ. The 260:230 ratio was 2.08 and the 260:280 ratio was 2.30. These values were similar to those reported for reovirus 3 virion RNA by Gomatos and Tamm, above.

The thermal transition midpoint (Tm) was determined by noting the % increase in optical density at 260 mμ with an increase in temperature. The Tm for Reo 3-RNA was measured in a 20 μg/ml solution of 0.15 M NaCl - 0.015 M sodium citrate, pH 7.0 and was found to be about 110° C. Heating the Reo 3-RNA in the presence of 2.76% formaldehyde depressed the Tm to 86° C. as expected for hydrogen-bonded helical polynucleotides. The capacity to induce interferon in rabbits was destroyed.

The Reo 3-RNA was not degraded by RNase under conditions which readily destroyed single-stranded yeast RNA, viz., 0.2 μg RNase/ml at 25° C. Reo 3-RNA was degraded very slowly on treatment with RNase at 10 μg/ml and at 56° C. temperature. The capacity to induce interferon was not impaired by treatment at 25° C. with the lower concentration of RNase. The Reo 3-RNA at 24 μg/ml was, however, rendered inactive by treatment at the high RNase level of 10 μg/ml at the elevated temperature of 56° C. and with longer incubation time of 2 hours.

The above demonstration of the failure of the noninfectious, nonreplicative form of single-stranded RNAs of viral origin including those of Newcastle Disease Virus, influenza A virus, and tobacco mosaic virus as well as the single-stranded polynucleotides to induce interferon lent further support to the concept of this invention that an essential requirement for interferon induction is a double or multistranding of RNA. The requirement for freedom from inhibitory protein or other inhibitory substances, as shown for PfI-RNA, and from capsid protein of reovirus type 3 virions is also to be emphasized.

(D) REPLICATIVE FORM OF RNA AND DNA

The invention involves the further discovery that replicative forms of RNA and DNA are interferon inducers. They should be in quite pure form and particularly free of inhibitory protein and/or other inhibitory substances.

The replicative form (RF) of RNA is a unique structure found in cells infected with RNA viruses. Bacteriophage (Bacterial viruses), and viruses which invade plants (including algae and other single-cell members of the plant kingdom) and viruses which invade animal cells are included in the scope of this invention. Examples of bacteriophage are coliphages MS2, M12, and R17. In some animal and plant viruses the replicative form and the RNA of the virus particle (virion) may be synonymous, e.g., reoviruses, wound tumor virus (plants), and rice dwarf virus (plants). This invention also includes the replicative form of DNA recently demonstrated in bacteriophage T4 and the replicative forms of other animal, bacterial, and plant DNA viruses.

Included in this invention are animal viruses of vertebrates, invertebrates, and so on down to simple single cell species such as protozoa. Included also in this invention are complexed polynucleotides prepared from polynucleotides containing ribose as well as those containing carbohydrates (e.g. deoxyribose, arabinose, other pentoses, hexoses, or any carbohydrate moiety). From this it is apparent that the source of the replicative form of DNA or RNA is immaterial and that its use as an interferon inducer is not dependent on the material from which it was purified.

The identifying characteristics of the (RF) of RNA have been published; a recent series of three articles appeared in *Bacteriological Reviews*, Vol. 30, No. 2, pages 267–307 under the title "Symposium on Replication of Viral Nucleic Acids" by Erikson and Franklin, by Shapiro and August and by Plagemann and Swim respectively. Important characteristics of the replicative forms are:

1. Resistance to digestion by pancreatic ribonuclease at 25° C. in 0.15 M sodium chloride.

2. High thermal stability, and thermal transition occurs over a narrow range of temperature.
3. Resistant to formaldehyde addition as evidenced by physical and biological data.

It has been stated above that RF-RNA is almost universally found in cells which have been infected with an RNA virus. For this reason the production and purification of one such replicative form will serve as an illustration of the use of other sources of this form of RNA. A suitable example of such a host-virus system is that of E. coli-MS2. The components of this system may be obtained from numerous repository sources. This virus is added to the E. coli cells undergoing uncubation so that the virus will invade and reproduce in the cells.

These infected E. coli cells are then removed from the culture broth as by centrifugation and they are then lysed by use of a detergent to release the RF which has been produced. The RF is then isolated by steps corresponding to those described above for the recovery of the RNA from *P. funiculosum*. In general, this involves a deproteinization step using phenol and removal of the phenol by extraction with a solvent such as ethyl ether. The nucleic acid is then precipitated by a known agent such as ethanol and the precipitate is recovered as by centrifugation. DNase and RNase are added to lyse undesirable fractions and ethanol is again added to obtain a precipitate. This precipitate can be reworked for further purification and it is then highly purified by chromatography. Suitable chromatographic materials are Sephadex and ecteola-cellulose.

The purified RF obtained in this manner is used to induce interferon production by known techniques, such as those described above. Assays for the interferon so produced are by known techniques such as those described above.

The purified RF itself is subjected to established analytical procedures to determine its identity as a replicative form of RNA. Suitable assay methods are described in the following articles:

Weissmann, C., Borst, P. Burden, R. H., Billeter, M. S., Ochoa, S., Proc. Natl. Acad. Sci.; 51:682 (1964).

Haselkorn, R., and Doty, P., J. Biol. Chem., 263:2738 (1961).

Billeter, M. A., Weissmann, C., Warner, R. C., J. Mol. Biol. 17:145 (1966).

Geiduschek, E. P., J. W. Moohr, and S. B. Weiss, Proc. Natl. Acad. Sci., 48:1078 (1962).

The following example describes a representative procedure:

EXAMPLE 9

Preparation of MS2 infected Escherichia coli cells

E. Coli Hfr 3000 was grown overnight on a reciprocal shaker at 37° C. in 200 ml. of broth as described by Weissmann, C., et al supra. 100 ml. of this culture was added to 1 liter of fresh broth and shaken for 2 hours at 37° C., at which time sufficient MS2 virus was added to infect the majority of E. coli cells. The infected culture was incubated by shaking at 37° C. for an additional time period (usually 1 hour) before addition of 2 ml. of chloroform and chilling in an ice bath. The infected cells were collected by centrifugation at 4000 rpm in the PR2 centrifuge for 15 minutes and washed once in sterile 0.06 M phosphate buffer at pH 7.0. The washed E. coli cell pack was stored at −20° C.

Isolation and Purification of MS2RNA(RF)

The method of Billeter et al, J. Mol. Biol., 17: 145 (1966), was used for the isolation procedure and is as follows:

1. The harvested, packed infected E. coli cells from one-liter batch were suspended in 16 ml. of 0.05 M TRIS - 0.1 M NaCl - 0.005 M ethylenediamine tetraacetate (EDTA) (this composition is known as TSE) and lysed by the addition of 2 ml. of 10% sodium dodecyl sulfate (SDS). After standing about five minutes at 30° C., lysis was completed.

2. The lysed cells were extracted with an equal volume of 88% phenol (previously washed three times with TSE buffer) at room temperature for five minutes. After centrifuging five minutes at 1500 rpm, the thick, viscous aqueous layer was removed with a Pasteur pipette. The phenol extraction was repeated twice more. The phenol was removed from the aqueous layer by extraction with ether five times at 5° C. Excess ether was removed by vacuum. The nucleic acid fraction was precipitated by 2 volumes of ethanol. After standing at least two hours at −20° C., the precipitate was centrifuged and dissolved in 18 ml. of 0.02 M TRIS - 0.005 M $MgCl_2$, pH 7.2

3. DNase was added at 20 μg/ml and digestion of the DNA fraction was carried out at room temperature for 30 minutes. After the addition of 2 ml. of 10X SSC, pancreatic RNase was added at 5 μg/ml and digestion of the RNA was continued for 30 minutes. The enzyme action was stopped by the addition of 0.033% (SDS). Two volumes of ethanol were added and precipitation was completed by standing at −20° C. overnight.

4. The precipitate was dissolved in 3 ml. of 0.015 M NaCl, 0.015 M Sodium citrate, pH 7.0 (SSC) and 0.1 mg. of purified hectorite (Macaloid) was added. Extraction with 2 volumes of phenol (equilibrated with SSC) was carried out at room temperature for five minutes. The phenol extraction with Macaloid addition each time was repeated 3 times and residual phenol was removed from the aqueous layer by 4 ether extractions. Excess ether was removed by vacuum and 2 volumes of ethanol were added. Precipitation was carried out at −20° C. overnight.

5. Exclusion chromatography on Sephadex G-200.

The precipitate was dissolved in 0.6 ml. of SSC and clarified by centrifugation at 2500 RPM for 20 minutes. The solution was applied to a column of Sephadex G-200 that was 1.5 × 25 cm. and equilibrated with SSC buffer. The void volume was previously determined by passing 0.5 ml. of a 0.2% solution of dextran blue through the column. The MS2RNA(RF) was eluted and occurred in the eluate fraction at the void volume. The single-stranded RNA and DNA digestion products remain on the Sephadex column.

6. Chromatography on Ecteola-cellulose

The pooled fractions containing MS2RNA(RF) from Sephadex G-200 exclusion chromatography were dialyzed against 0.01 M sodium phosphate buffer, pH 7. The dialyzed material was applied to a 0.9 × 3 cm column of ecteola-cellulose. The column was washed successively with 10 ml. of 0.01 M Sodium phosphate - 0.2 M NaCl and 40 ml. of 0.01 M. Phosphate - 0.4 M NaCl. The MS2RNA(RF) was eluted in 10 ml. of 0.01 M sodium phosphate - 0.6 M NaCl.

The methods of interferon induction, interferon assay and interferon characterization are as described above. They were applied in the present instance with the following results.

Characterization of the MS2RNA(RF)

A. Relative resistance of MS2RNA(RF) to ribonuclease

The above obtained MS2RNA(RF) was treated with RNase at pH 7.0 and the resulting degradation of the RNA was followed by measuring the increase in optical density with the recording spectrophotometer equipped with a controlled heater compartment maintaining the temperature.

The MS2RNA(RF) at 25 μg/ml was resistance to RNase at 0.25 μg/ml at 25° C. and 56° C. However, with RNase at 10 μg/ml. and 56° C. a slow linear degradation of MS2RNA was achieved. Single-stranded yeast ribosomal RNA in the amount of 20 μg/ml was used as a comparative control and it showed a very rapid degradation in 3 to 4 minutes with 0.25 μg/ml. RNase/ml at 25° C.

The capacity of MS2RNA(RF) after various conditions of RNase treatment to induce interferon in rabbits is demonstrated in Table XXI.

TABLE XXI

Sensitivity of Biological Activity of MS2RNA(RF) to Various Treatments

| Treatment | MS2RN (RF) (16 μg/ml) Concentration | Temp. (° C) | Time (minutes) | Titer of Interferon induced in rabbits |
|---|---|---|---|---|
| Ribonuclease | 0.25 μg/ml | 25° | 30 | 160, 640 or > |
| Untreated control | — | " | " | 10, 640 or > |
| Ribonuclease | 10 μg/ml | 56° | 2 hrs. | <5, <5 |
| Untreated control | — | " | " | 10, 80 |
| Formaldehyde | 2.76% | 100° | 1°/min. incre.* | <5, <5 |
| Untreated control | — | " | " | 40, 160 |
| High temperature | — | 110° | 5 min.** | <5, <5 |
| Untreated control | — | — | — | 320, 320 |
| Nil (control) | — | — | — | <5, <5 |

*1°/min. increase to 100° C.
**Followed by rapid cooling to prevent renaturation.

Whereas MS2RNA(RF) treated with 0.25 μg RNase/ml. showed no reduction in capacity to induce interferon, a similar sample lost inducing capacity after treatment with 10 μg RNase/ml at a higher temperature for a longer period of time. Thus as shown in Table XXI, the biological activity was destroyed by treating with 10 μg/ml of ribonuclease at 56° C. but not with 0.25 μg/ml at 25° C. Heating to 100° C. in 2.76% formaldehyde irreversibly destroyed the interferon inducing activity. Inducing capacity was also destroyed by heating the RNA to 110° C. to effect transition of the helix to a random coil, and rapid cooling to prevent reformation of the helix as indicated by failure to reverse the hyperchromic effect. These characteristics are similar to those found for double-stranded HeI-RNA and Reo 3-RNA.

B. Ultraviolet Absorption Spectrum

The ultraviolet absorption spectrum of the purified MS2RNA(RF) was determined using a Beckman DB-G recording spectrophotometer. The curve was typical for nucleic acid with minimum at 230 mμ and maximum at 257.5 mμ. The 257:230 ratio was 2.36 and the 260:280 ratio was 2.36.

C. Thermal Stability

Thermal denaturation of MS2RNA(RF) was measured in experiments performed using a Beckman DB-G spectrophotometer equipped with a Tm analyzer and recorder. In SSC buffer the MS2RNA(RF) underwent a sharp thermal transition with the midpoint (Tm) at 110° C. This sharp thermal transition and the high Tm are characteristics usually associated with double-stranded molecules with relatively high thermal stability.

Heating of MS2RNA(RF) in the presence of 2.76% formaldehyde effected a 60% increase in absorbancy, with a Tm at 86° C. According to Haselkorn and Doty, J. Biol. Chem., 236, 2738, 1961, the addition of formaldehyde to double-stranded RNA yields a product with lower thermal stability. There was no decrease in absorbancy upon reannealing, indicating inhibition of helix formation.

D. Effectiveness as interferon inducer

The ability of the MS2RNA(RF) to induce the production of interferon in animals was demonstrated by its administration to rabbits. The rabbits were bled and the serum subjected to the assay tests described above and recognized in the art for this purpose. The tests and their results are set forth in Tables XXII, XXIII and XXIV.

TABLE XXII

Species Specificity of MS2RNA(RF) Induced Rabbit Serum Interferon

| Interferon Titer Based on Assay in Cell Cultures | | |
|---|---|---|
| Homologous Cells | Heterologous Cells | |
| Primary Rabbit Kidney | Mouse Embryo | Chick Embryo |
| 640 | ND | <20 |
| 640 | ND | <20 |
| 320 | ND | <10 |
| 512 | <8 | ND |

ND = Not done

TABLE XXIII

Trypsin Sensitivity of MS2RNA(RF) Induced Rabbit Serum Interferon*

| Expt. No. | Treatment | Interferon Titer on RK-13** cell monolayers |
|---|---|---|
| 1 | None | 8 |
|  | Crystalline Trypsin (50 μg/ml, 4 Hr. at 35° C) | <2 |
| 2 | None | 128 |
|  | Crystalline Trypsin (50 μg/ml, 4 Hr. at 35° C) | <2 |

*Partially purified by chromatography on CM-Sephadex.
**RK-13 cells are a stable line of rabbit kidney cells.

TABLE XXIV

Physical Characteristics of MS2RNA(RF) Induced Rabbit Serum Interferon

| Source of Interferon | Inducer | Isoelectric Point | Molecular Weight* |
|---|---|---|---|
| Rabbit Serum | MS2RNA(RF) | 6.56-7.20 | 52000 + 167000 |

*Molecular weight determined by gel filtration through G-100 Sephadex. This method yields molecular weight with accuracy ± 10%.

To demonstrate that animals which are given the interferon inducer MS2RNA(RF) are in fact protected against a subsequent challenge virus infection, a standard test was carried out. This is given in Table XXV.

TABLE XXV

Induction of Resistance to Pneumonia virus of mice (PVM) Infection in Mice by MS2RNA (RF).

| Total Dose of MS2RNA (RF) per animal | No. survived Total No. Infected | % Survival | Excess % Survival | Mean Survival Time in Days |
|---|---|---|---|---|
| 18 μg | 17/20 | 85.0 | 73.6 | >14 |
| 0 (control) | 4/35 | 11.4 | 0.0 | 8 |

The comparative interferon inducing ability of MS2RNA(RF) and other substances is shown in Table XXVI.

TABLE XXVI

Interferon Inducing Capacity for Rabbits of MS2RNA(RF) and of Other Preparations Derived from the E. Coli-MS2 Coliphage System

| Material injected into rabbits | Intravenous dose per rabbit | Interferon titer of rabbit serum |
|---|---|---|
| MS2RNA(RF) (double-stranded, replicative form) | 8 μg | 160, 40 |
|  | 2 μg | 20, 10 |
|  | 0.5 μg | <10, <10 |
| MS2-VF-RNA (single-stranded, virion derived) | 8 μg | <10, <10 |
| MS2 virions** | $1.1 \times 10^{11}$ PFU/ml* | <10, <10 |
| Uninfected E. coli** RNA | 100 μg | <10, <10 |
| Nil (control) | — | <10, <10 |

*Purified virus.
**Prepared by known procedures.

As with the other double-stranded RNA inducers described above, serum interferon was detectable about 1 hour after RNA injection, reached a peak after 2 to 4 hours and declined by 6 hours.

The above example describes an E. coli-MS2 system and is to be considered as illustrative of other examples using different host cells which are infected with different RNA viruses. This is also true of double-stranded DNA of the replicative form.

A determination was made of the ability of the MS2RNA(RF) to induce interferon in monolayers of primary rabbit kidney cell cultures. The cell culture monolayers were incubated for 18 hours with medium containing MS2RNA(RF). Inteference with vesicular stomatitis virus replication was measured by plaque reduction assay. As little as 0.04 μg of the RNA effected 50% plaque reduction.

A summary showing a comparison of the biological activities of the various multi-stranded polynucleotide and RNA's of diverse origin is given in Table XXVII. All were active in less than microgram amount in inducing interferon in rabbits and resistance to viral infection in cell culture. The larger amounts of the various RNA's used in the mouse protection experiments were highly active in inducing resistance in mice, but do not represent the minimal required dose for stimulating such activity.

TABLE XXVII

Summary of Biological Activities of Double-Stranded RNA's of Diverse Origin

| RNA injected | Minimal effective amount | | Protective dose in mice against virus | | |
|---|---|---|---|---|---|
| | Interferon induction in rabbits | Interference to VSV in rabbit kidney cell culture | PVM | Col. Sk | Sendai** |
| Synthetic | | | | | |
| Polyinosinic-polycytidylic (I:C complex) | 0.5 µg | 0.00125 µg | 7.9 µg | 131 µg | 16 µg*** |
| Viral | | | | | |
| Reovirus 3 (Reo 3-RNA) | 0.5 µg | 0.04 µg | 16 µg*** | ND**** | ND |
| Coliphage (MS2-RF-RNA) | 0.5 µg | 0.04 µg | 18 µg | ND | ND |
| Fungal | | | | | |
| Penicillium funiculosum (HeI-RNA) | 0.125 µg | 0.3 µg*** | 20 µg | 50 µg | ND |

*Minimal required dose not determined
**Sendai strain parainfluenza 1 virus was given by nasal challenge.
***Not previously reported.
****ND = Not done.

Table XXVII shows the relative activity of the inducers of this invention and the following table XXVII the exceptional activity of the I:C complex in protecting mice against varying amounts of a challenged PVM dose.

TABLE XXVIII

Level of Efficacy of Induced Host Resistance to Pneumonia Virus of Mice

| I:C Dose Intranasal | Virus Challenge in LD$_{50}$ | % Survival | Mean Days |
|---|---|---|---|
| 15.7G µg | 10,000 | 93.3 | >14.0 |
| " | 3,150 | 73.3 | >14.0 |
| " | 1,000 | 86.7 | >14.0 |
| " | 315 | 100 | >14.0 |
| " | 100 | 93.3 | >14.0 |
| " | 31.5 | 100 | >14.0 |
| None | 10,000 | 0 | 5.0 |
| " | 3,150 | 3.3 | 6.0 |
| " | 1,000 | 0 | 6.0 |
| " | 315 | 0 | 7.0 |
| " | 100 | 6.6 | 7.0 |
| " | 31.5 | 3.3 | 7.0 |

E. UTILITY IN HUMANS

The above animal experiments show the effectiveness of the agents used in this invention, to induce interferon in animals for prophylactic and therapeutic protection against infection. The effectiveness of the complexed polymers I:C to induce interferon in tussue cultures of human cells was investigated. Roller tube cultures of human embryonic kidney cells were incubated overnight at 35° C. with medium containing I:C. After removal of this medium, the treated cultures were challenged with sufficient virus to infect all cultures, incubated at 33° C., and observed for evidence of cytopathic effects for up to seven days. The minimum effective concentration of I:C was that concentration which showed 100% suppression of viral cytopathic effect in 50% or more of the tube cultures.

Roller tube cultures treated with I:C, but not challenged with virus, were observed for evidence of toxicity. No evidence of toxicity was observed. The results are given in Table XXIX.

TABLE XXIX

| Challenge Virus | Minimum Effective Concentration (µg/ml) |
|---|---|
| Rhino 1 | 2.6 – 5.24 |
| " 11 | 3.25 or less |
| " 20 | 3.25 or less |
| " 42 | 0.8 or less |
| " 47 | 0.8 or less |

As an indication of the use of the interferon inducers of this invention to augment interferon production in humans the following examples are presented:

EXAMPLE 10

Oral-nasal preparation

As a propylactic intranasal preparation against respiratory viruses such as the common cold, a dose of from 1 to 100 milligrams of complexed polymer I:C would be applied to the nasal and oral membranes every 2 to 3 days. This period of administration is due to the prolonged duration of the induced interferon.

The application could be by way of an aqueous suspension in an aspirator spray so that one or two sprays would deliver about 5 to 10 milligrams. Or, an aerosol preparation using conventional fluorochlorohydrocarbons as propellants could be prepared and used. Additionally, the preparation could be applied as a nose drop pharmaceutical liquid.

This preparation would also be used therapeutically about every 2-3 days in cases of actual respiratory infection. An observing physician may decide that a more frequent (such as daily) or a less frequent (as every 4th day) may be indicated.

One of the other inducers of this invention could replace the I:C of this example having in mind their relative activity as discussed above and in Table XXVII.

EXAMPLE 11

Eye Preparation

For prophylactic and therapeutic use in the eyes, a conventional eye drop preparation such as sterile peanut oil is made up so that a single drop would contain from 1 to 100 milligrams of the complex polymer I:C or one of the other above inducers. A single drop would be applied to the eye every 2 to 3 days.

The drops would be applied for its therapeutic activity to an eye infected with Herpes, Adenovirus and Vaccinia and also infected with Trachoma. It would be applied to the noninfected eye as a prophylactic protection at the same time.

A conventional eye ointment would be prepared so that the small amount ordinarily applied would contain from 1 to 100 milligrams of the I:C. This ointment could be a polyethylene-liquid petrolatum gel, for instance.

EXAMPLE 12

Cutaneous preparation

For application to the skin in abraded areas, the interferon inducer can be added to conventional bases for ointments, creams, lotions or liquid preparations so that one gram contains from 1 to 100 milligrams of I:C for example. It would be applied every 2 to 3 days.

EXAMPLE 13

Sterile injection

Representative of a preparation for parenteral administration is a conventional sterile oily or aqueous solution or suspension, such as physiological saline. One cc. of this would contain from 1 to 100 milligrams of the selected interferon inducer of this invention, and it would be injected every 2 to 3 days in cases of viral infection.

We claim:

1. The method of stimulating the production of species-specific interferon in living animal cells which involves subjecting said cells to the species-specific interferon inducing effect of a doublestranded polynucleotide in the substantial absence of an inhibiting factor wherein said doublestranded polynucleotide is a synthetic chemically defined non-toxic, non-antigenic, non-replicating polymer resulting from the complexing of 1:1 molar ratios, with respect to their bases, of polyinosinic acid and polycytidylic acid, which themselves are synthetic, and each lacking the capacity to induce the production of species-specific interferon.

2. The method according to claim 1 in which the cells are contained in a nutrient culture medium.

3. The method according to claim 1 in which the cells are those of a living animal or human.

* * * * *

UNITED STATES PATENT OFFICE
CERTIFICATE OF CORRECTION

Patent No. 4,124,702　　　　　　　　Dated November 7, 1978

Inventor(s) G. P. Lampson, A.A. Tytell, A.K. Field, M.R. Hilleman

It is certified that error appears in the above-identified patent and that said Letters Patent are hereby corrected as shown below:

Col. 5, l. 68 -- "stored" should read --scored--

Col. 7, l. 64 -- "by" should read --but--

Col. 9, Table VII, l.43 -- "21 16" should read -- <16--

Signed and Sealed this

Eleventh Day of March 1980

[SEAL]

Attest:

SIDNEY A. DIAMOND

Attesting Officer　　　　Commissioner of Patents and Trademarks